United States Patent [19]

Irvin

[11] 4,000,044
[45] Dec. 28, 1976

[54] FRACTIONATION OF IMMISCIBLE LIQUIDS OF EQUAL DENSITY

[75] Inventor: Howard B. Irvin, Bartlesville, Okla.

[73] Assignee: Phillips Petroleum Company, Bartlesville, Okla.

[22] Filed: July 9, 1974

[21] Appl. No.: 486,755

[52] U.S. Cl. .................... 203/14; 203/69; 203/39; 203/70; 260/621 A; 203/17; 203/18
[51] Int. Cl.² ............... B01D 3/34; C07B 5/00
[58] Field of Search ............... 203/69, 14, 18, 17, 203/68, 70; 260/621 R, 621 A, 621 L, 621 D, 621 G, 586 R, 586 P

[56] References Cited

UNITED STATES PATENTS

| | | | |
|---|---|---|---|
| 2,286,056 | 6/1942 | Brown | 203/69 |
| 2,573,244 | 10/1951 | Bogart et al. | 203/69 |
| 2,729,599 | 1/1956 | Ohsol et al. | 203/69 |
| 2,745,882 | 5/1956 | Hale | 203/18 |
| 2,762,760 | 9/1956 | Walker | 203/69 |
| 3,509,028 | 4/1970 | Budd et al. | 203/69 |

OTHER PUBLICATIONS

L. H. Horsley, *Azeotropic Data III*, 1973, pp. 28, 29, 31, 33–35.

*Primary Examiner*—Jack Sofer

[57]. ABSTRACT

Separation by distillation and formation of immiscible liquid phases of nearly equal densities which comprises distilling a mixture containing the same in the presence of an added liquid of substantially different density, preferentially soluble in a recycle to the distillation zone and having a volatility under conditions of distillation such that it will vaporize preferentially to a liquid desired to be retained in the distillation zone to be removed as bottoms therefrom, e.g., toluene added to produce gravity separation of a heavy water-rich phase and a light phase containing phenol, cyclohexanone and cyclohexylbenzene and the added toluene which is used as reflux to the drying column in the overall process in which cyclohexanone and phenol are produced from cyclohexylbenzene.

6 Claims, 1 Drawing Figure

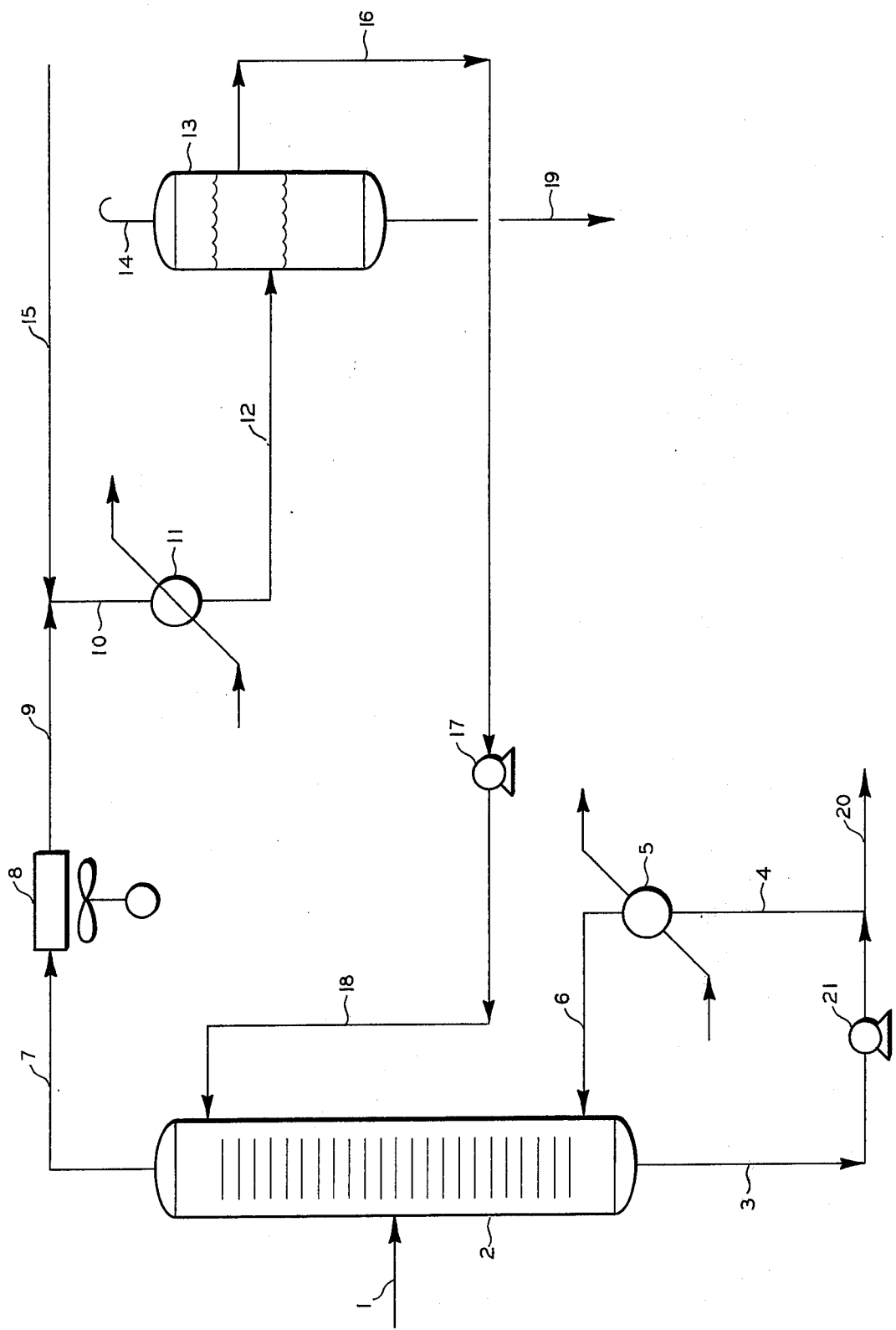

FRACTIONATION OF IMMISCIBLE LIQUIDS OF EQUAL DENSITY

This invention relates to the fractionation of liquids that form immiscible liquid phases of substantially equal density at ambient conditions. More particularly, it relates to the use of an additive liquid in the separation by fractionation or distillation of immiscible liquids of equal density.

In one of its concepts the invention provides a method for the separation by distillation or fractionation of liquids of equal density by performing the distillation and consequent phase separation in the presence of a liquid of substantially different density, said liquid being preferentially soluble in the liquid phase to be recycled to the distillation and being more volatile than other components of the recycled liquid phase. In another of its concepts the invention provides a process for the separation of water from organic compounds, e.g., the drying of a mixture of phenol, cyclohexanone and cyclohexylbenzene as obtained, for example, in the production of cyclohexanone from cyclohexylbenzene. In a still further concept of the invention it provides a process or method in which a selected hydrocarbon, e.g., toluene, methylcyclohexane, and/or dimethylcyclopentane is used as herein described to separate in a distillation or fractionation column water from a mixture containing phenol, cyclohexanone and cyclohexylbenzene; the toluene or other added liquid, upon phase separation, containing components desirably returned to the column and being recycled to the column, e.g., as reflux therefor.

By liquids of "equal density" is meant individual components of equal density in liquid state or liquid mixtures which under the conditions of operation are of such nearly equal densities that their separation by liquid phase formation and decantation cannot be readily accomplished on any practical basis. For example, in dehydrating a mixture containing phenol, cyclohexanone and cyclohexylbenzene, as obtained from the production of cyclohexanone from cyclohexylbenzene, by fractionation in a column, it is found that the overhead vapors contain a relatively high concentration of phenol and cyclohexanone by virtue of the azeotropic distillation taking place. Upon condensing and attempting to settle the phases which are formed, it is found that the organic and the water phases are not distinct or of such character that a practical, worthwhile liquid density separation can be accomplished by decanting. To recycle even a portion of the water phase to the column as a recycle or reflux stream will of course result in very inefficient fractionation. Thus, a method is needed to separate the organic phase from the water phase so that the former may serve as reflux to the fractionation.

It has now occurred to me that the addition of an organic compound such as toluene, to the system, e.g., into the column at an appropriate point or into the condensed overhead or into another location so that it will be present in the formation and/or accumulation steps of the liquid phases and therefore, will not only considerably repress the presence of phenol and cyclohexanone in the overhead vapors but will produce readily separable liquid phases, the phase containing toluene, phenol and cyclohexanone being returnable to the column as a recycled stream or as overhead reflux therefor. Further, my concept provides that the water phase, now readily separable, upon being discharged from the process, will contain considerably reduced concentrations of phenol and cyclohexanone. Further, only a very small concentration of toluene will be present in the liquid, water rich phase.

It is an object of this invention to provide a method for the separation of at least partially immiscible liquids of substantially equal density as said liquids are herein defined. It is another object of this invention to reduce the quantity of non-desired reflux or recycle to a column or distillation zone in which liquids or liquid mixtures of equal or nearly equal densities are being distilled. It is a still further object of this invention to provide selected additive liquids for the distillation, phase separation and recovery of liquids of equal or nearly equal densities. Further still it is an object of this invention to provide an efficient dehydration process. Still another object of the invention is to provide a process for the removal of water from a mixture containing it together with phenol, cyclohexanone and cyclohexylbenzene.

Other aspects, concepts, objects and the several advantages of the invention are apparent from a study of this disclosure, the drawing and the appended claims.

According to the present invention there is provided a method for the separation by distillation and phase formation of liquids of nearly equal densities which comprise distilling the same in the presence of an added liquid of substantially different density, preferentially soluble in a recycle stream to the distillation zone and having a volatility under the conditions of distillation such that it will vaporize preferentially to the liquid desired to be retained in the distillation zone and to be removed therefrom as bottom product.

The invention will now be described as it is applicable to the separation of water in a fractionation operation. More specifically, it will be described with respect to the separation of water from a mixture containing it, phenol, cyclohexanone and cyclohexylbenzene.

Referring now to the drawing the feed from which water is to be removed is passed by 1 into fractionator 2 from which dehydrated bottoms product is removed by 3 which is in part passed by 4 through heater 5 and back to the column by 6 to provide reboiling heat input. The column bottom is operated at about 20 psia and the bottom temperature is maintained at about 440° F. The top of the column is at about 18 psia and is maintained at a temperature of about 200° F. Overhead is taken off by 7, cooled by air cooler 8 and passed by 9 and 10 through condenser 11 and by 12 to phase separator 13 from which gases may be vented by 14 as needed. Toluene which, according to the invention, has been added to the process as through a make-up conduit 15, or otherwise, causes, according to the invention, a neat separation of the two liquid phases and the lower density liquid phase comprising toluene, phenol and cyclohexanone is passed by 16 and pump 17 by 18 into column 2 as reflux therefor. The higher density liquid phase comprising principally water containing relatively small concentrations of phenol, cyclohexanone and toluene is removed at 19 as fractionator-dehydrator overhead product.

The following tabulations have been calculated to show the improvement obtained by operating according to the invention.

| Equipment Specifications | | | |
|---|---|---|---|
| Drying Column 2 | After Cooler 11 | Reflux Pump 17 | Bottoms Pump 21 |
| 8' Diam. × 100' | 1000 Sq.Ft. | 125gpm, 5hp | 7600gpm |
| 45 Sieve Trays | 2.5mm BTU/hr | | 150hp |
| Air Fin Condenser 8 | Phase Separator 13 | Reboiler 5 | |
| 2240 Sq.Ft. | 5' Diam. × 20' | 3660 Sq.Ft. | |
| (Bare tube basis) | | 29.3mm BTU/hr | |
| 17.9mm BTU/hr | | | |

TABLE I

EXAMPLE ACCORDING TO INVENTION
Material Balance in Pounds/Hr.

| Stream No. | 1 | 7–9 | 16–18 | 19 | 20 | 15 |
|---|---|---|---|---|---|---|
| Water | 10,000 | 9,975 | 25 | 9,950 | 50 | |
| Toluene | 4 | 49,875 | 49,870 | 5 | | 1 |
| Phenol | 26,714 | 55 | 50 | 5 | 26,709 | |
| Cyclohexanone | 29,042 | 102 | 100 | 2 | 29,040 | |
| $C_{12}$Cyclics | 353,484 | | | | 353,484 | |
| Heavies | 4,692 | | | | 4,692 | |
| Total, LBS/HR | 423,937 | 60,007 | 50,045 | 9,962 | 413,975 | 1 |
| GPM | 940 | 138 | 118 | 20 | 920 | |
| Density at 100F, LBS/Cu.Ft. | | | 53.00 | 62.03 | | |

TABLE II

EXAMPLE - WITHOUT INVENTION
Material Balance in Pounds/hr.

| Stream No. | 1 | 7–9–12 | 16–18 | 19 | 20 |
|---|---|---|---|---|---|
| Water | 10,000 | 14,480 | 4,530 | 9,950 | 50 |
| Phenol | 26,714 | 6,832 | 6,315 | 517 | 26,197 |
| Cyclohexanone | 29,042 | 7,428 | 7,255 | 173 | 28,869 |
| $C_{12}$Cyclics | 353,484 | | | | 353,484 |
| Heavies | 4,692 | | | | 4,692 |
| Total, LBS/Hr. | 423,932 | 28,740 | 18,100 | 10,640 | 413,292 |
| GPM | 940 | 58 | 36 | 22 | 918 |
| Density at 100F, LBS/Cu.Ft. | | | 62.14 | 62.19 | |

It is readily apparent from Table I that stream 16–18 is readily separable from stream 19 by liquid phase settling, while in Table II these streams are virtually of the same density and considerable entrainment of each in the other would be encountered in a practical situation even with a very large, quiescent settling vessel 13 being employed.

In the absence of toluene (or other equivalent liquid found to be operative in a specific situation), as evident from information given above, the water phase would contain much more phenol and cyclohexanone and the hydrocarbon phase would contain much more water. If these two liquid phases were separated, which would be difficult and impractical as is evident from data presented above and later herein, the water phase would contain about 58 times as much organics as when toluene is used. This would either result in much greater losses of organics from the process and greater water effluent pollution problems or more equipment and expenses necessary to recover organics from the water phase.

EXPERIMENTAL BASIS

The following three liquid mixtures were prepared and placed in capped glass bottles:

| SOLUTION | A | B | C |
|---|---|---|---|
| Component | wt.% | wt.% | wt.% |
| Water | 50.4 | 25.2 | 16.6 |
| Phenol | 23.8 | 11.9 | 0.1 |
| Cyclohexanone | 25.8 | 12.9 | 0.2 |
| Toluene | 0 | 50.0 | 83.1 |
| | 100.0 | 100.0 | 100.0 |

Solution A represents the Drying Column overhead without toluene; Solution B is Solution A diluted 50% with toluene; and Solution C is the estimated column overhead composition with toluene being refluxed to the Drying Column. Note in the latter case, the level of phenol and cyclohexanone are very low because the toluene suppresses these components to the bottom of the column.

Observation on Solution A

1. The mixture was shaken vigorously and allowed to settle at room temperature (75° F). Fine dispersions were formed that slowly separated with the water phase on the top. After 16 hours the water phase was clear, but the organic phase was hazy.

2. The bottles was heated to 150° F in a water bath. The phases inverted with the water on the bottom. Both phases were clear and separated fairly rapidly.

3. The bottle was slowly cooled to room temperature. The phases started to invert at about 117° F and inversion was complete at about 93° F. The temperature at which about half the organics moved to the bottom of the bottle was 100° F. Both phases were milky. In the 93°–117° F range, large globs of organic floated around randomly in the water phase.

Observations on Solution B

1. Shaken vigorously and allowed to settle at room temperature. Rapidly separated into two clear phases, water on the bottom.

2. Heated to 158° F in water bath. Did not invert, both phases clear.

3. Cooled to room temperature. Did not invert. Phases were cloudy, particularly the water phase. Phases cleared up after temperature stabilized at 75° F.

Observation on Solution C

Same as for Solution B, but not heated above room temperature.

Conclusions

1. Without the addition of a fourth component, it would be impossible to separate the phases by gravity at 100° F, the temperature planned for acceptable commercial operations.
2. The addition of toluene gives sharp separation by gravity settling in the temperature range of 75°–150° F.
3. To minimize loads on other equipment, the column overhead should be cooled as much as practical to give low levels of dissolved organics in the water phase and dissolved water in the organic phase. Refrigerated cooling could not be economically justified under present circumstances.
4. As Solution A is heated, more phenol that cyclohexanone dissolves in the water phase. Since phenol is more dense than water and cyclohexanone is less dense than water, the water phase increases in density relative to the organic phase causing the inversion.
5. The addition of toluene causes the organic phase to be lighter than the water phase throughout the temperature range because its density is appreciably less than that of the other three components and practically all of it goes into the organic phase.

The added liquid now preferred is toluene. Aromatic hydrocarbon liquids of 6–7 carbon atoms to the molecule are preferred. In addition to toluene, benzene, cyclohexane, methylcyclohexane, dimethylcyclopentanes are considered to be well operative. Also, n-hexane and n-heptane can be used. Toluene is now preferred at least for the reason that its toxicity is low relative to that of benzene.

Reasonable variation and modification are possible within the scope of the foregoing disclosure, drawing, and the appended claims to the invention the essence of which is that the separation of liquids of approximately equal or equal densities by distillation or fractionation is accomplished in the presence of an added liquid of substantially different density. This liquid is preferentially soluble in material to be recycled to the distillation zone and has a volatility under the conditions of the distillation such that it will vaporize preferentially from the desired bottoms liquid components.

I claim:

1. A method for the dehydration of feedstock containing water, phenol, cyclohexanone, cyclohexylbenzene and hydrocarbons heavier than cyclohexylbenzene, said feedstock capable upon distillation of forming a distillate of water also containing phenol and cyclohexanone as immiscible liquid components of the distillate mixture said method comprising:
   1. distilling the feedstock in the presence of an added liquid chosen from among toluene benzene, methylcyclohexane, dimethylcyclopentanes, cyclohexane, n-hexane, and n-heptane, said added liquid introduced into the overhead from the distillation column before condensing said overhead;
   2. condensing said distillate admixed with said added liquid forming thereby a distillate liquid that is phase separable into a water phase and a phase comprising said added liquid, phenol, and cyclohexanone;
   3. separating said phase comprising said added liquid, phenol, and cyclohexanone from said water phase;
   4. recycling said phase comprising said added liquid, phenol, and cyclohexanone to the distillation;
   5. removing water, substantially free of phenol and cyclohexanone; and
   6. recovering phenol, cyclohexanone, cyclohexylbenzene and heavier hydrocarbons substantially free of water, from the kettle of the distillation.

2. A method according to claim 1 wherein the phase separated and returned to said distillation zone is returned thereto as reflux therefor.

3. A method according to claim 1 wherein the added liquid is toluene.

4. A method according to claim 1 wherein the added liquid is benzene.

5. A method according to claim 1 wherein the added liquid is chosen from among methylcyclohexane, dimethylcyclopentanes, and cyclohexane.

6. A method according to claim 1 wherein the added liquid is chosen from among n-hexane and n-heptane.

* * * * *